(12) United States Patent
Griffin et al.

(10) Patent No.: US 9,319,805 B2
(45) Date of Patent: *Apr. 19, 2016

(54) NOISE REDUCTION IN AUDITORY PROSTHESES

(71) Applicant: Cochlear Limited, Macquarie University, NSW (AU)

(72) Inventors: Kyriaky Griffin, Kellyville (AU); Michael Goorevich, Naremburn (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,132

(22) Filed: Apr. 29, 2015

(65) Prior Publication Data

US 2015/0319544 A1 Nov. 5, 2015

Related U.S. Application Data

(63) Continuation of application No. 12/743,542, filed as application No. PCT/AU2008/000426 on Mar. 26, 2008, now Pat. No. 9,049,524.

(30) Foreign Application Priority Data

Mar. 26, 2007 (AU) ................. 2007901596

(51) Int. Cl.
*H04R 25/00* (2006.01)
*A61N 1/36* (2006.01)

(52) U.S. Cl.
CPC .............. *H04R 25/50* (2013.01); *H04R 25/356* (2013.01); *A61N 1/36032* (2013.01); *H04R 25/407* (2013.01); *H04R 25/505* (2013.01); *H04R 2225/43* (2013.01)

(58) Field of Classification Search
CPC .. H04R 25/40; H04R 25/405; H04R 2225/43; H04R 25/50; H04R 25/505; G10L 21/0208; G10L 21/0205
See application file for complete search history.

(56) References Cited

U.S. PATENT DOCUMENTS

| | | | | |
|---|---|---|---|---|
| 4,156,116 A * | 5/1979 | Yanick | ................ | H03G 11/002 381/106 |
| 4,536,888 A * | 8/1985 | Wilson | ................ | H04M 1/6025 379/347 |
| 4,759,071 A * | 7/1988 | Heide | .................. | H04R 25/356 327/552 |
| 4,887,299 A * | 12/1989 | Cummins | ............ | H04R 25/356 381/106 |
| 5,369,711 A * | 11/1994 | Williamson, III | ... | H03G 3/3026 381/104 |
| 5,485,515 A * | 1/1996 | Allen | ....................... | H04B 1/64 379/391 |
| 5,553,151 A * | 9/1996 | Goldberg | ............... | H03G 7/002 381/312 |
| 5,631,968 A * | 5/1997 | Frey | ....................... | H03G 7/002 333/14 |
| 6,151,400 A * | 11/2000 | Seligman | ........... | A61N 1/36032 381/101 |
| 6,757,395 B1 * | 6/2004 | Fang | ................... | G10L 21/0208 381/94.3 |
| 6,970,570 B2 * | 11/2005 | Goldstein | ............ | H04R 25/356 381/106 |
| 7,009,533 B1 * | 3/2006 | Wegener | ................ | H04N 1/413 341/76 |
| 7,171,008 B2 * | 1/2007 | Elko | ...................... | H04R 3/005 381/122 |
| 7,206,421 B1 * | 4/2007 | Taenzer | ................ | H04R 3/005 381/119 |
| 7,688,990 B2 * | 3/2010 | Hellgren | ................ | H04R 25/43 381/312 |
| 8,249,861 B2 * | 8/2012 | Li | ........................... | G10L 21/02 381/316 |
| 8,290,181 B2 * | 10/2012 | Stokes, III | ............ | H03G 3/301 381/102 |

(Continued)

*Primary Examiner* — Matthew Eason

(57) ABSTRACT

A method of processing audio signals for an auditory prosthesis is provided. The method includes a noise reduction step and a later compression step. A gain control step is provided prior to the compression step. The gain control step operates so as to minimize the occurrence of signal compression in the compression step. An auditory prosthesis arranged to provide the method is also provided.

20 Claims, 5 Drawing Sheets

(56) References Cited

U.S. PATENT DOCUMENTS

| | | | |
|---|---|---|---|
| 9,049,524 B2 * | 6/2015 | Griffin | H04R 25/356 |
| 2002/0015503 A1 * | 2/2002 | Hou | H04R 3/00 |
| | | | 381/94.3 |
| 2002/0128830 A1 * | 9/2002 | Kanazawa | G10L 21/0208 |
| | | | 704/226 |
| 2003/0198357 A1 * | 10/2003 | Schneider | G10L 21/0208 |
| | | | 381/94.2 |
| 2005/0111683 A1 * | 5/2005 | Chabries | H03G 9/005 |
| | | | 381/317 |
| 2010/0177915 A1 * | 7/2010 | Latzel | H04R 25/356 |
| | | | 381/312 |
| 2012/0263329 A1 * | 10/2012 | Kjeldsen | H03M 1/185 |
| | | | 381/315 |

* cited by examiner

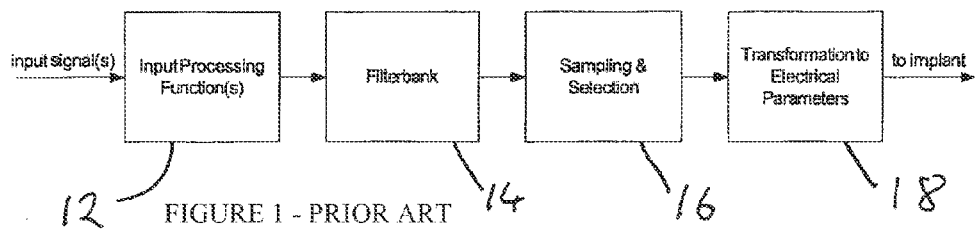
FIGURE 1 - PRIOR ART
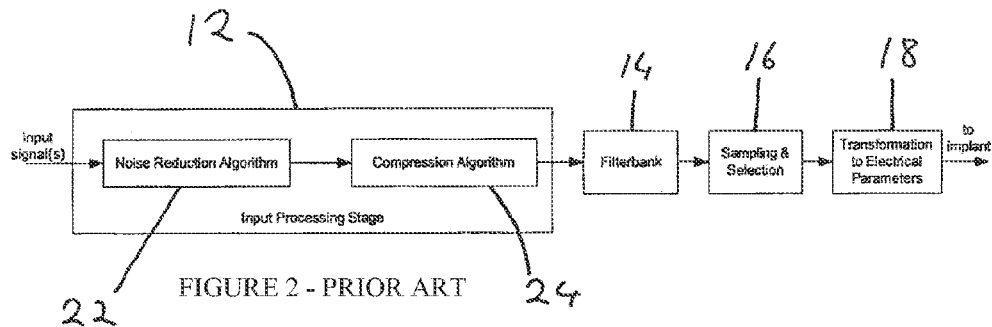
FIGURE 2 - PRIOR ART
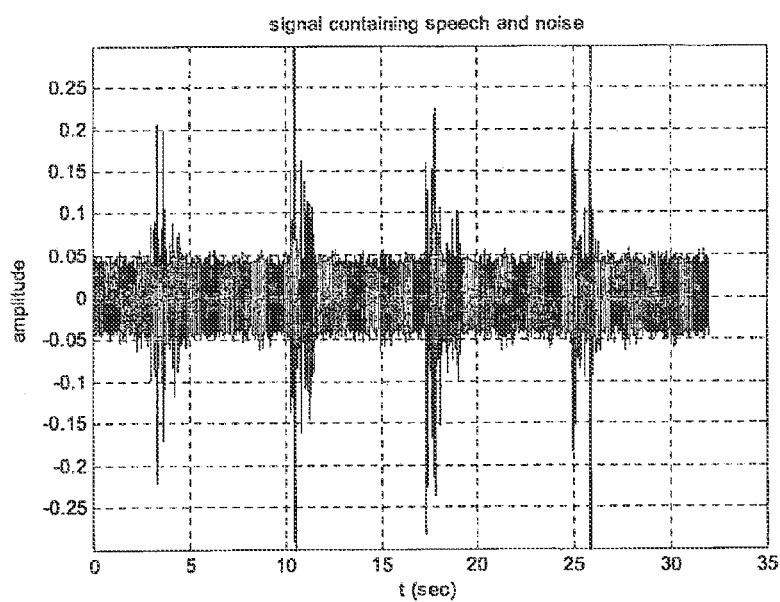
FIGURE 3

NOISE REDUCTION IN AUDITORY PROSTHESES

CROSS-REFERENCE TO RELATED APPLICATIONS

This is a continuation of U.S. patent application Ser. No. 12/743,542 filed on Oct. 4, 2010, which is a national stage application of International Application No. PCT/AU2008/000426 filed on Mar. 26, 2008, which claims priority from Australian Provisional Patent Application No. 2007901596, filed on Mar. 26, 2007. The contents of each of these applications are hereby incorporated by reference.

BACKGROUND

1. Field of the Invention

The present invention relates to improvement of the signal to noise ratio in auditory prostheses, including cochlear implants and other devices.

2. Related Art

Auditory prostheses are reliant upon high quality audio signals being used for processing. This applies to devices of all types, including cochlear implants, middle ear implants, implanted and non-implanted hearing aids, electro acoustic devices (having electrical and acoustic stimulators) and other such devices. An important measure of signal quality is the signal to noise ratio, or SNR.

Noise reduction algorithms have been shown to provide some benefit to cochlear implant recipients exposed to selective environmental noises. Many recipients using such algorithms still experience difficulty in understanding speech in mildly to very noisy environments, for example where many people are speaking at a party or gathering. As a result, some recipients avoid such social situations where they expect they will have a very poor understanding of speech. In particular, it has been observed that recipients do not experience the expected advantage in performance in noisy environments from their noise reduction algorithms. It is an object of the present invention to improve the noise reduction processes within auditory prostheses.

SUMMARY OF THE INVENTION

Embodiments of the present invention broadly point provides an arrangement where additional gain control is provided prior to the compression stage, the signal level being controlled in order to minimize the occurrence of signal compression. As a consequence, the output to the rest of the signal path has an improved SNR, as the signal is compressed less often by the compression stage.

According to one aspect, embodiments of the present invention provide a method of processing audio signals for an auditory prosthesis, the method including a noise reduction step and a later compression step, wherein a gain control step is provided prior to the compression step, the gain control step operating so as to minimize the occurrence of signal compression in said compression step.

According to another aspect, embodiments of the present invention provide an auditory prosthesis including an audio processor, the audio processor including a noise reduction stage and a subsequent compression stage, the audio processor further including a gain control stage prior to the compression stage, the gain control stage operatively minimizing the occurrence of signal compression in said compression stage.

It has been determined by the inventors that the conventional arrangement of compression following noise reduction has the effect of worsening the SNR, since the compressed signal has a lower relative difference between the peaks of the speech components and the peaks of the noise components. By providing additional gain control, the need to operate the compressor in the compression region is minimised, thereby retaining much of the SNR benefit of the noise reduction stage.

BRIEF DESCRIPTION OF THE DRAWINGS

Illustrative embodiments of the present invention are described herein with reference to the accompanying figures, in which:

FIG. 1 is a block diagram of a typical prior art sound processor signal path;

FIG. 2 is a block diagram of a typical prior art input processing stage;

FIG. 3 is a graph for a signal of time against amplitude for mixed speech and noise;

DETAILED DESCRIPTION

Figure 4:
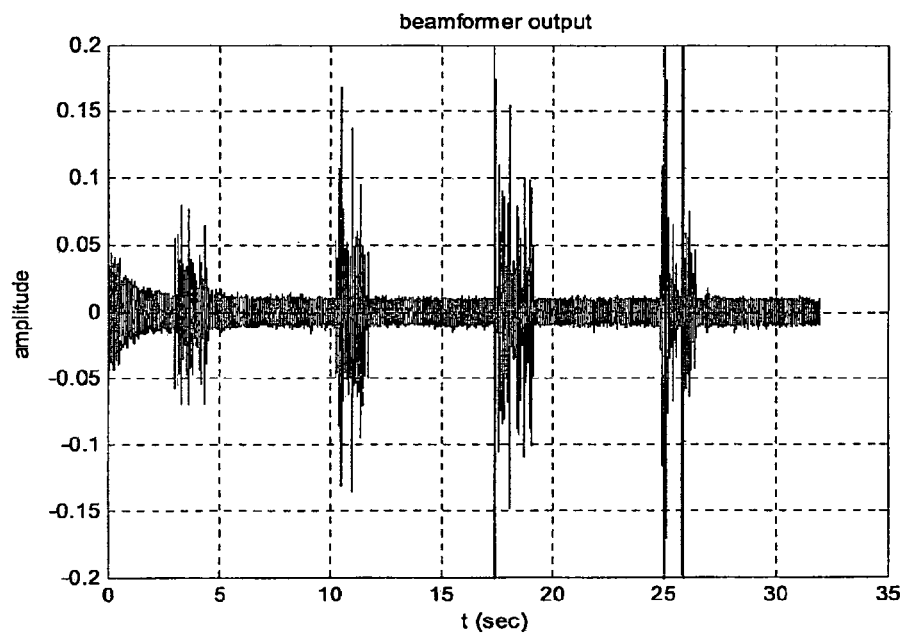
FIG. 4 is a graph of the same signal after noise reduction processing.

Embodiments of the present invention will be described primarily with respect to an implementation suitable for use with implanted devices, such as intracochlear implants. However, embodiments of the present invention is applicable to other types of hearing prostheses, particularly those employing noise reduction algorithms or processing. Such prostheses include middle ear implants, implanted and non-implanted hearing aids, electro acoustic devices (having electrical and acoustic stimulators), brain stem and other neural stimulators, and other such devices.

A typical prior art signal path in a cochlear implant (CI) sound processor is shown in FIG. 1. The input sound signals (typically from a microphone) are first subjected to input processing functions 12. These may consist of one or more input processing algorithms, whose function may be for example to reduce noise in the signal, optimize the gain of the signal, perform compression on the signal and so forth. Following input processing 12, the signals are presented to a filterbank 14. The filterbank 14 may be based on an FFT implementation, a band of HR filters, or any other suitable arrangement. The filterbank 14 operates so as to determine the amplitude of the components of the signal within predefined frequency channels. The channels are typically selected to match the logarithmic nature of frequencies for hearing perception, and may be discrete or overlapping channels. The filterbank 14 outputs are then presented to the sampling and selection function 16, and then to a transformation (mapping) function 18 which transforms the magnitude and frequency of the signal into electrical parameters suitable for the implant.

Of course, for different types of prosthesis, the stages may differ somewhat in their nature and function. However, for any auditory prosthesis, quality of the audio signal, and the quality of the output of the input processing functions, is critical to maximizing SNR. FIG. 2 illustrates a signal path where the input processing stage 12 consists of a noise reduction algorithm 22 followed by a compression algorithm 24. This is a common arrangement in a CI sound processor. Noise reduction algorithms are desirable to attempt to maximize the intelligibility of the speech percept of the recipient by improving the SNR. Noise is any type of signal that the recipient does not want to listen to, and therefore as well as general environmental noise it may include competing speech signals. The result at the output of the noise reduction algorithm 22 is generally an increase in the SNR, and an improvement in SNR will in principle correspond directly to an improvement in speech intelligibility.

Compression algorithms 24 are necessary in sound processor signal paths to prevent loud sounds from clipping and causing distortion. The compression algorithm 24 reduces loud sounds in amplitude, but otherwise preserves the signal during the compression periods. If the compression algorithm 24 is not present in the signal path, then clipping will result elsewhere in the signal path.

For example, the loudness growth or mapping function is typically part of the transformation of the audio signal into electrical parameters for stimulation. It compresses the wide input dynamic range of the sound processor to the limited electrical dynamic range available to the recipient via the implant. However, when signals become large, they will simply be clipped at the recipient's most comfortable level (C level), and amplitude modulation information will be lost as all large signals will be presented at the same, maximum level to the user. This is most undesirable and highlights the importance of having a compression algorithm 24 in the signal path of a CI system.

Figure 7:
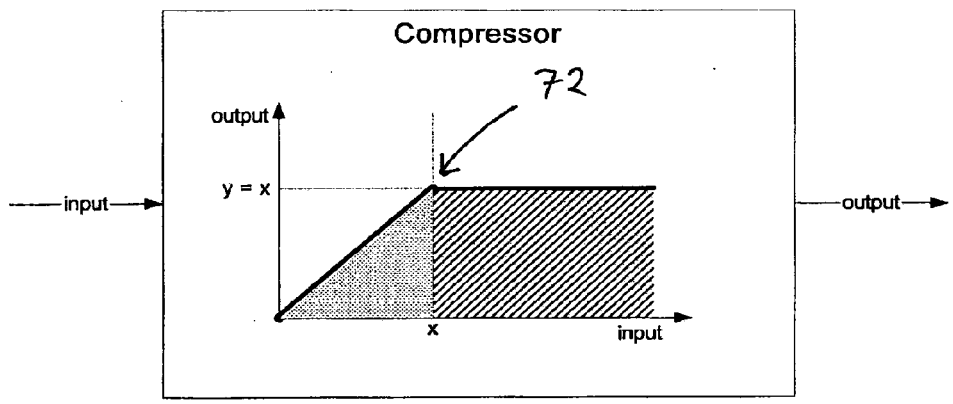
FIG. 7 is a graph of input against output, illustrating the operation of a compressor.

Fast acting compression over short periods of time such as a syllable of speech has been shown to be beneficial in this situation. These algorithms typically operate only above a pre-defined level, known as the compression threshold or kneepoint 72. FIG. 7 illustrates the input/output characteristics of a typical compressor. The input signal is progressively 'compressed' in dynamic range, so that the signals are not clipped by the following processing stages. Different parameters being chosen for the compressor will result in a different output curve for the compressor, and therefore different levels where the output is scaled to a fixed value, different threshold levels below which compression does not operate, and a different value for the maximum output level. FIG. 7 shows a compressor with an infinite compression ratio, so that regardless of how large the input to the compressor becomes above the kneepoint 72, the output is fixed to a predetermined level. However, the compressor may have a different compression ratio, depending upon the requirements of the application.

A problem with compression arises when the input sound is of a high intensity for an extended period of time. This is a typical scenario in noisy sound environments, which are also characterized by elevated speech levels for audibility over the noise. Such an environment can cause the compression algorithm 24 to continuously operate in compression (as the signal is always above the threshold), particularly during the elevated speech periods. It has been discovered that this is a highly undesirable effect in the case of speech embedded in noise, as a reduction in SNR will occur. When the CI signal path contains a noise reduction algorithm 22 preceding the compression algorithm 24, the benefit the noise reduction algorithm 22 provides in SNR is then counteracted by compression in the signal path.

Figure 5:
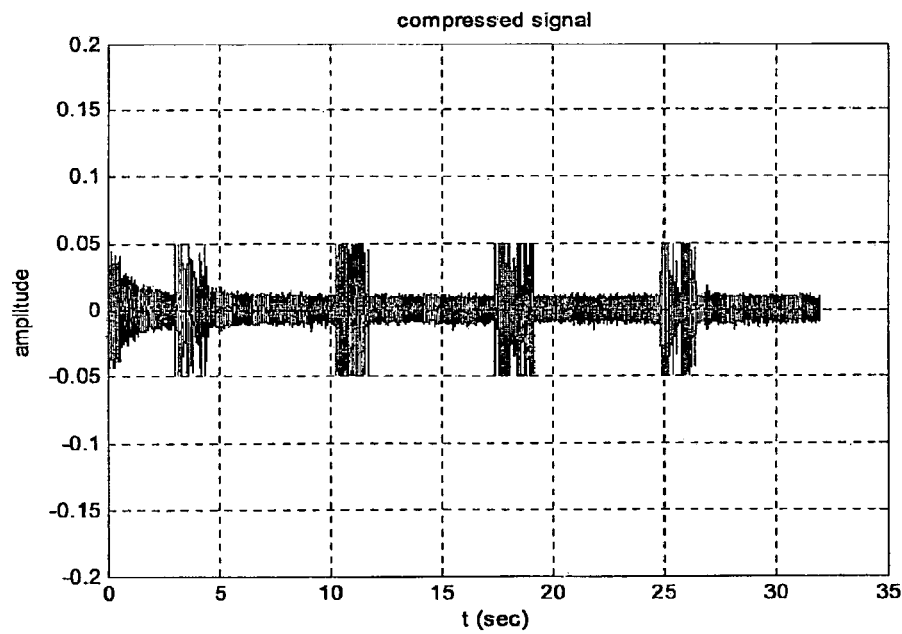
FIG. 5 is graph of the processed signal illustrating compression.

To understand why compression in noisy environments reduces the SNR, we will consider, with reference to FIGS. 3 to 5, a signal as it progresses through the input processing stage 12 of the sound processor depicted in FIG. 2. In this example, the noise reduction algorithm 22 is a beamforming algorithm. The signal contains a desired speech component mixed with an unwanted noise component, and is shown in raw, unprocessed form in FIG. 3. This signal is processed by a noise reduction algorithm 22, a dual microphone array beamformer, whose output is shown in FIG. 4.

The improvement in SNR that the beamformer has provided is very clear when comparing FIG. 4 to FIG. 3, looking particularly at the relative difference in amplitude between the peaks in the speech components relative to the noise components. The output of the beamformer (i.e. the signal of FIG. 4) is then fed into the compression algorithm 24. The compression algorithm 24 (similar to that shown in FIG. 7) has a 1:1 slope below its compression threshold 72, and provides infinite compression above its threshold 72. This is of course only an example of one possible compression characteristic. If the amplitude of the output signal of the beamformer exceeds the compression threshold 72 at any instant in time, the signal will be compressed, as shown in FIG. 5. Note that in this example, the compressor is only compressing the speech components as the noise components have been significantly reduced by the beamformer, and lie below the compressor's threshold 72. Thus, the effect of compression is to reduce signal, whilst leaving noise unaffected.

Comparing the peaks of the signal during the speech segments before (FIG. 4) and after (FIG. 5) compression, it is evident that the output of the compression algorithm 24 has lower peaks in the speech segments. Therefore the relative difference between the peaks of the speech segments and those of the noise segments of the compressed signal is smaller, corresponding to a smaller SNR than that of the original signal output from the noise reduction algorithm 22. If the compression algorithm 24 is continually compressing the speech segments of the signal, then it is reducing the improvement in the SNR which was provided by the beamformer, which is clearly a very undesirable effect.

The following embodiments of the present invention seek to avoid this outcome by either integrating gain control into the noise reduction algorithm 22, or providing gain control at the output of the beamforming algorithm or elsewhere along the signal path prior to the compression function 24. The noise reduction algorithm 22 for this purpose may be any algorithm that attempts to reduce the noise component relative to the signal component, typically after' estimating the signal and noise components. The gain control function is preferably automated so that it can continually adjust the signal levels to avoid the compression region of the compressor 24.

Figure 6:
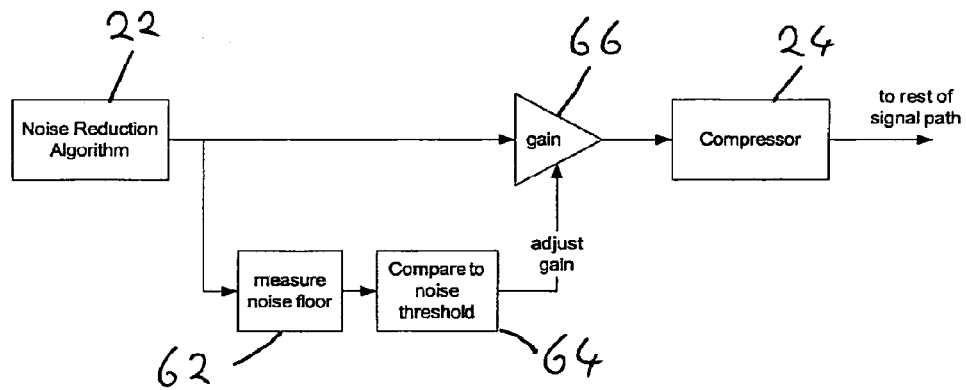
FIG. 6 is a block diagram of one implementation of the present invention.

FIG. 6 illustrates one embodiment of the present invention, in which gain control is provided at the output of the noise reduction processing 22. The input stage shown in FIG. 6 incorporates a noise floor estimator 62, which generates a measure of the noise floor in the received sound signal. The noise floor is then compared to a predetermined noise threshold 64, which is related to the compressor 24 parameters. If the noise floor is above the threshold then the gain is reduced on the amplifier 66. Conversely, if the noise floor is below the threshold, the gain is increased. Consequently, the variation in gain modifies the signal level before it is presented to the compressor 24. It has been found that the gain control at the output of the noise reduction stage 22 operates so as to minimize the need for signal compression, and so maximize the improvement in SNR that the noise reduction algorithm 22 has provided in a noisy environment. The noise reduction algorithm 22 may be, for example, the beamformer arrangement disclosed in U.S. Pat. No. 6,888,949 by Vanden Berghe, or US patent application No 2004/0252852 by Taenzer, the disclosures of which are hereby incorporated by reference, or any other desired noise reduction algorithm.

The noise floor estimation 62 and comparison 64 arrangement may be the arrangement disclosed, for example, in commonly assigned U.S. Pat. No. 6,151,400, the disclosure of which is incorporated herein by reference.

Many other embodiments of the present invention are possible, a few examples of which appear below. All the embodiments described below assume the compressor 24 has an input-output characteristic of some sort, an example of which is shown in FIG. 7. In practical tests, a compressor design employing a kneepoint 72 of 7ObB SPL and fast attack time of 5 ms, with infinite compression past the kneepoint 72, has been used. Note that any numbers provided in the descriptions of the embodiments serve as examples only, and are not restricted to the given values.

Figure 8:
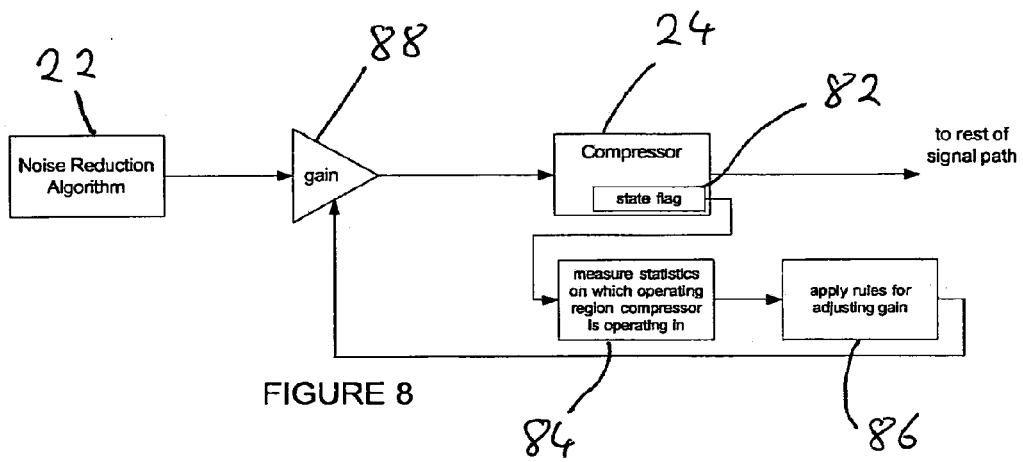
FIG. 8 is a block diagram of another implementation of gain control according to embodiments of the present invention.

FIG. 8 shows one example of gain control being used to maintain the SNR of the output signal of a noise reduction algorithm 22. In this example, the state of the compressor 24—that is whether it is operating in or out of compression—is monitored by a "state flag" 82. Although this can be implemented in various ways, in a simple form the flag 82 indicates TRUE when the compressor 24 is in compression and FALSE when it is not. The "state flag" 82 will toggle back and forth from TRUE to FALSE during the course of operation of the compressor 24. A function 84 is then provided that measures statistics based on the value of the "state flag" 82. Using a set of rules 86 derived from the statistics measured, a gain 88 is applied to the noise reduction algorithm's output signal.

Figure 9:
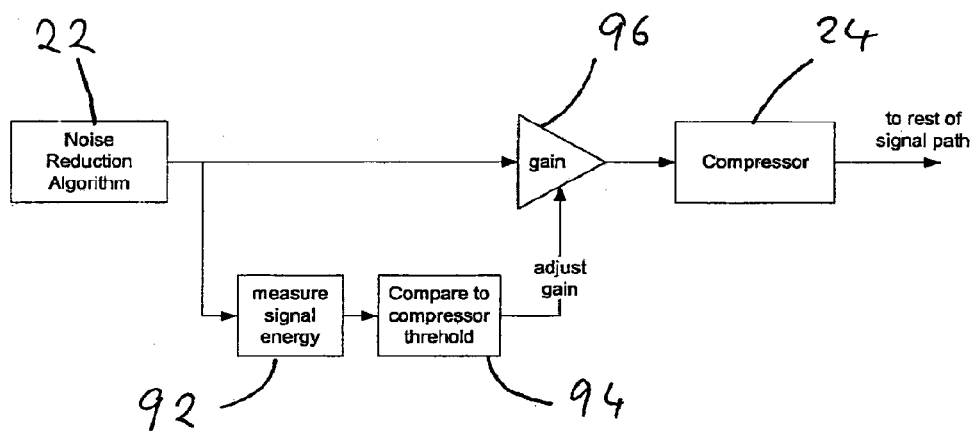
FIG. 9 is a block diagram of further implementation of embodiments of the present invention.

FIG. 9 shows another embodiment of the present invention. In this example, a measurement of the energy or power 92 in the noise reduced signal is made, and then compared 94 to the expected threshold or kneepoint 72 value of the compressor 24. If the measurement of energy or power 92 is above the threshold 72 the gain 96 is reduced, if below the threshold 72 the gain 96 is increased. The energy/power measurement 92 is made over a predetermined time interval, with increases in gain 96 made more gradually than decreases in gain 96.

Figure 10:
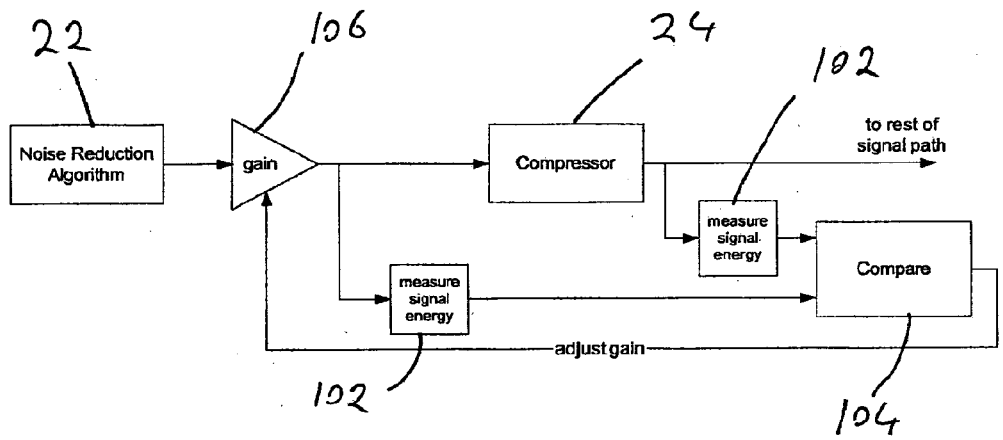
FIG. 10 is a block diagram of another implementation of embodiments of the present invention.
Figure 11:
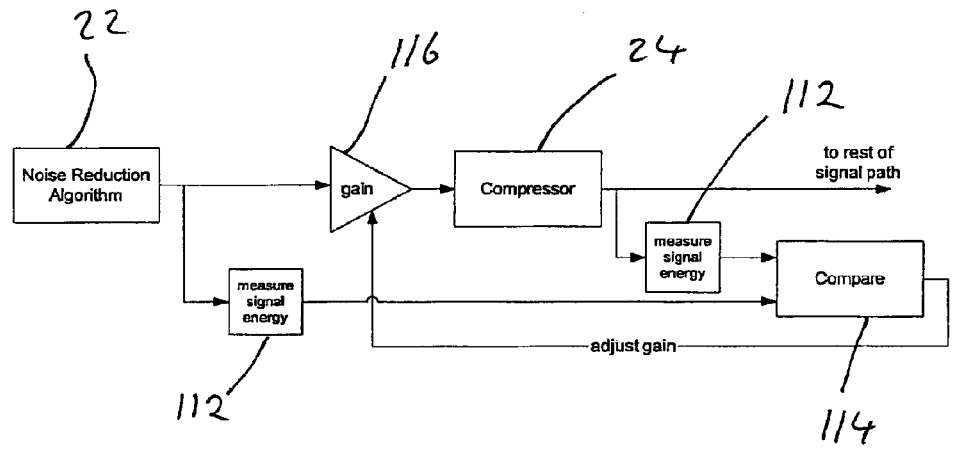
FIG. 11 is a block diagram of another implementation of embodiments of the present invention.

FIG. 10 and FIG. 11 show another example of gain control. In these examples, a measurement of the signal energy/power 102, 112 of the noise reduced signal is made before and after the compressor 24, and then compared 104, 114 to each other. If the signal energy after compression is less than that before compression, the gain 106, 116 is reduced; otherwise if roughly equal the gain 106, 116 remains unchanged.

Figure 12:
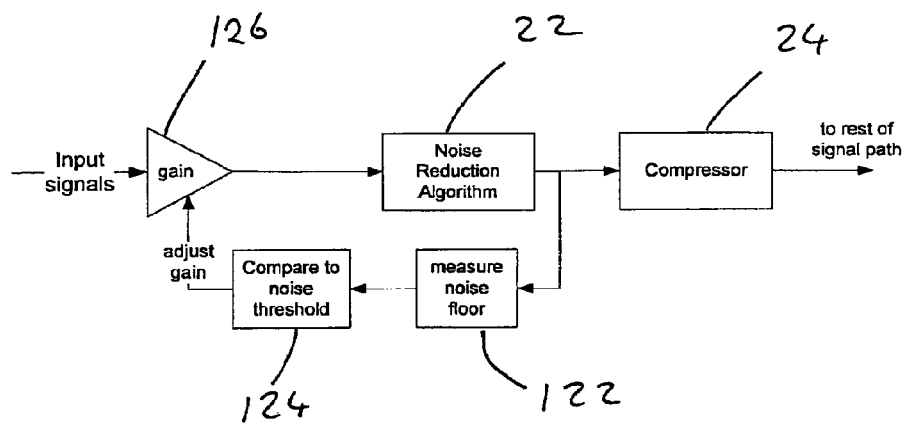
FIG. 12 is a block diagram of another implementation of embodiments of the present invention.

FIG. 12 illustrates an embodiment where the additional gain control is provided before the noise reduction algorithm 22. The output of the noise reduction algorithm 22 is used to determine a noise floor 122, and this value is compared to a noise threshold 124, similar to the arrangement described with reference to FIG. 6. The comparison is used to adjust the gain 126 applied to the input signals. In this way, the gain is adjusted to control the level output by the noise reduction algorithm 22, and accordingly input to the compressor 24. It will be appreciated that the same principle could be applied to any of the other examples, modified to use a feedback path taken from after the noise reduction block.

It will be appreciated that although various, alternatives have been disclosed, the present invention is capable of implementation in many other arrangements. Additional features, alternatives and variations are possible within the scope of the present invention.

As an example, in alternative embodiments some or all of the functional steps could be provided after the filterbank 14 (i.e. in the frequency domain). The noise reduction 22, gain and compression 24 stages may all be performed after the filterbank 14 of FIG. 1. Alternatively, the noise reduction stage 22 may be provided before the filterbank 14, while the gain and compression 24 stages are provide after the filterbank 14. Furthermore, the stages themselves may be split into multiple stages provided before and after the filterbank 14. For example, part of the compression stage 24 may be located before the filterbank 14 and part after. Similarly, the gain stage could be provided as two gain stages, one before the filterbank 14 and one after. Potentially, more than one filterbank 14 can be provided in the overall signal path. It should be understood that compression is achieved by applying gain to a signal with appropriate time constraints. Since gain (i.e. multiplication) is a linear mathematical operation, successive applications of gain on a signal can be applied in one step, by first combining the multiplicative factors. Hence, conceivably, the steps of gain followed by compression could be achieved in one operation, with the appropriate time constraints of each operation taken into account before combining.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method of processing an audio signals by an auditory prosthesis, the method including:
    processing the audio signal to at least one of (i) increase a signal-to-noise ratio (SNR) of the audio signal or (ii) apply a noise reduction algorithm to the audio signal;
    after processing the audio signal, compressing the audio signal when an energy of the audio signal exceeds a threshold energy level; and
    applying a gain to the audio signal, wherein the gain limits a change in the SNR of the audio signal resulting from the compression step.

2. The method of claim 1, wherein the audio signal includes a speech portion and a noise portion, wherein the noise-reduction step comprises reducing an energy of the noise portion of the audio signal, and wherein the gain-control step comprises adjusting a gain applied to each of the noise portion of the audio signal and to the speech portion of the audio signal.

3. The method of claim 1, wherein applying the gain to the audio signal occurs after increasing the SNR of the audio signal and before compressing the audio signal.

4. The method of claim 1, wherein applying the gain to the audio signal comprises:
    after the increasing the SNR of the audio signal, measuring a noise floor of the audio signal;

increasing the gain applied to the audio signal when the measured noise floor is threshold. low; and decreasing the gain applied to the audio signal when the measured noise floor is threshold high.

5. The method of claim 1, wherein compressing the audio signal comprises limiting the energy of the audio signal to the maximum energy.

6. The method of claim 1, wherein applying the gain to the audio signal comprises:

after the increasing the SNR of the audio signal, measuring the energy of the audio signal;

increasing the gain applied to the audio signal when the energy of the audio signal is threshold low; and decreasing the gain applied to the audio signal when the energy of the audio signal is threshold high.

7. The method of claim 6, wherein measuring the energy of the audio signal occurs over a predetermined time interval, and wherein increases in the gain occur more gradually than decreases in the gain.

8. The method of claim 1, wherein applying the gain to the audio signal and compressing the audio are implemented in a single step.

9. The method of claim 1, wherein applying the gain to the audio signal comprises adjusting the gain applied to the audio signal so as to maintain at a constant value the SNR of the audio signal before compression and after compression.

10. The method of claim 1, wherein applying the gain to the audio signal comprises:

after the increasing the SNR of the audio signal, measuring a first energy of the audio signal;

after compressing the audio signal, measuring a second energy of the audio signal; and decreasing the gain applied to the audio signal when the first energy of the audio signal is greater than the second energy first energy.

11. A method of processing an audio signal by an auditory prosthesis, the method comprising:

processing an audio signal to at least one of (i) increase a signal-to-noise ratio (SNR) of the audio signal or (ii) apply a noise reduction algorithm to the audio signal;

after the processing of the audio signal, compressing the audio signal when an energy of the audio signal exceeds an energy level; and applying a gain to the audio signal, wherein the gain minimizes the occurrence of the audio signal exceeding the energy level.

12. The method of claim 11, wherein the audio signal includes a speech portion and a noise portion, wherein the noise-reduction step comprises reducing an energy of the noise portion of the audio signal, and wherein the gain-control step comprises adjusting a gain applied to each of the noise portion of the audio signal and to the speech portion of the audio signal.

13. The method of claim 11, wherein applying the gain to the audio signal occurs after increasing the SNR of the audio signal and before compressing the audio signal.

14. The method of claim 11, wherein applying the gain to the audio signal comprises:

after the increasing the SNR of the audio signal, measuring a noise floor of the audio signal;

increasing the gain applied to the audio signal when the measured noise floor is threshold low; and decreasing the gain applied to the audio signal when the measured noise floor is threshold high.

15. The method of claim 11, wherein compressing the audio signal comprises limiting the energy of the audio signal to the maximum energy.

16. The method of claim 11, wherein applying the gain to the audio signal comprises:

after the increasing the SNR of the audio signal, measuring the energy of the audio signal;

increasing the gain applied to the audio signal when the energy of the audio signal is threshold low; and decreasing the gain applied to the audio signal when the energy of the audio signal is threshold high.

17. The method of claim 16, wherein measuring the energy of the audio signal occurs over a predetermined time interval, and wherein increases in the gain occur more gradually than decreases in the gain.

18. The method of claim 11, wherein applying the gain to the audio signal and compressing the audio are implemented in a single step.

19. The method of claim 11, wherein applying the gain to the audio signal comprises adjusting the gain applied to the audio signal so as to maintain at a constant value the SNR of the audio signal before compression and after compression.

20. The method of claim 11, wherein applying the gain to the audio signal comprises:

after the increasing the SNR of the audio signal, measuring a first energy of the audio signal;

after compressing the audio signal, measuring a second energy of the audio signal; and decreasing the gain applied to the audio signal when the first energy of the audio signal is greater than the second energy first energy.

* * * * *